United States Patent [19]

Vold et al.

[11] Patent Number: 5,561,049
[45] Date of Patent: Oct. 1, 1996

[54] METHOD FOR DETECTING ANTIBODIES

[75] Inventors: Barbara S. Vold, Menlo Park; Harshvardhan B. Mehta, Fremont; Edwin F. Ullman, Atherton, all of Calif.

[73] Assignee: Behringwerke AG, Marburg, Germany

[21] Appl. No.: 310,028

[22] Filed: Sep. 21, 1994

[51] Int. Cl.$^6$ .................. G01N 33/538; G01N 33/542; G01N 33/543; G01N 33/564
[52] U.S. Cl. .................. 435/7.1; 435/7.4; 435/7.9; 435/7.91; 435/7.92; 435/7.93; 435/962; 435/971; 435/975; 436/506; 436/518; 436/537; 436/541
[58] Field of Search .................. 435/7.1, 7.4, 7.9, 435/7.91, 7.92, 7.93, 962, 971, 975; 436/506, 518, 537, 541

[56] References Cited

U.S. PATENT DOCUMENTS

| | | | |
|---|---|---|---|
| 3,654,090 | 4/1972 | Schuur et al. | 435/7 |
| 3,720,760 | 3/1973 | Bennich et al. | 436/573 |
| 4,020,151 | 4/1977 | Bolz et al. | 436/527 |
| 4,024,235 | 5/1977 | Weetall et al. | 435/5 |
| 4,062,935 | 12/1977 | Masson et al. | 435/7.7 |
| 4,143,124 | 3/1979 | Masson, et al. | 436/509 |
| 4,184,849 | 1/1980 | Cambiaso et al. | 436/523 |
| 4,279,617 | 7/1981 | Masson et al. | 436/523 |
| 4,687,732 | 8/1987 | Ward et al. | 435/6 |
| 4,855,242 | 8/1989 | Soeldner et al. | 436/539 |
| 5,200,318 | 4/1993 | Rabin et al. | 435/7.21 |

FOREIGN PATENT DOCUMENTS

| | | |
|---|---|---|
| 8930242 | 8/1984 | Australia . |
| 070527A1 | 1/1983 | European Pat. Off. . |
| 168689A2 | 1/1986 | European Pat. Off. . |
| 0353895A1 | 2/1990 | European Pat. Off. . |
| 410893A2 | 1/1991 | European Pat. Off. . |
| 0524502A2 | 1/1993 | European Pat. Off. . |
| WO90/07117 | 6/1990 | WIPO . |
| WO92/05446 | 4/1992 | WIPO . |

OTHER PUBLICATIONS

Nakawaka, et al., CHEMICAL ABSTRACTS, vol. 119:25, (Dec. 20, 1993), p. 724, "Development of a method of detecting anti–glutamic acid decarboxylase (GAD) antibodies in the sera of patients with IDDM using 125–I–labeled rate GAD".

Nakamura, et al., "Current Concepts and Diagnostic Evaluation of Autoimmune Disease", *Arch Pathol Lab Med*(1988) vol. 112, pp. 869–877.

Atkinson, et al., "64 000 M, autoantibodies as predictors of insulin–dependent diabetes", *Lancet*(1990) vol. 335, pp. 1357–1360.

van Erp, et al., "Application of a Sol Particle Immunoassay to the Determination of Affinity Constants of Monoclonal Antibodies", *Journal of Immunoassay*(1991) vol. 12, No. 3, pp. 425–443.

"Syn$^{elisa}$ GAD II–Antibodies" (Elisa USA, Inc.).

*Primary Examiner*—David Saunders
*Attorney, Agent, or Firm*—Shelley G. Precivale; Theodore J. Leitereg

[57] ABSTRACT

This invention pertains to methods to detect antibodies in a sample. The methods use an amount of antigen that is up to 1000, preferably 10–100 times the minimum amount antigen that can be reliably detected and that is less than the maximum expected amount of antibodies in the sample. An antigen:antibody complex is formed and becomes bound to a binding agent that does not bind free antigen. The free antigen is then detected as a measure of antibodies present in the sample.

39 Claims, No Drawings

METHOD FOR DETECTING ANTIBODIES

BACKGROUND OF THE INVENTION

1. Field of the Invention

Detection of antibodies is a useful tool in the diagnosis of diseases caused by antigens. Detection of autoantibodies is also useful in determining a patient's risk of developing a disease. There has been much research relating to detecting autoantibodies as a risk factor for patients developing insulin dependent diabetes mellitus ("IDDM"). There are numerous autoantibodies that are believed to be indicative of IDDM, which is also known as Type I Diabetes or juvenile diabetes. These include insulin autoantibodies, pancreatic islet cell antigen autoantibodies, and most recently autoantibodies to the 65 kd isoform of glutamic acid decarboxylase ("$GAD_{65}$").

Autoantibodies to $GAD_{65}$ have been suggested to be one of the earliest markers for the development of IDDM. These autoantibodies are present several years before clinical onset of IDDM, at which time intervention steps could be taken to deter the progression of the disease.

2. Description of the Related Art

Specific antibodies can only be measured by detecting binding to their antigen or a mimic thereof. Although certain classes of immunoglobulins containing the antibodies of interest may in some cases be separated from the sample prior to the assay (Decker, et al., EP 0,168,689 A2), in all assays, at least some portion of the sample immunoglobulins are contacted with antigen. For example, in assays for specific IgM, a portion of the total IgM can be adsorbed to a surface and the sample removed prior to detection of the specific IgM by contacting with antigen. Binding is then measured by detection of the bound antibody, detection of the bound antigen or detection of the free antigen.

For detection of bound antibody, a labeled anti-human immunoglobulin or labeled antigen is normally allowed to bind antibodies that have been specifically adsorbed from the sample onto a surface coated with the antigen, Bolz, et al., U.S. Pat. No. 4,020,151. Excess reagent is washed away and the label that remains bound to the surface is detected. This is the procedure in the most frequently used assays, or example, for hepatitis and human immunodeficiency virus and for numerous immunohistochemical tests, Nakamura, et al., *Arch Pathol Lab Med* 112:869–877 (1988). Although this method is relatively sensitive, it is subject to interference from non-specific binding to the surface by non-specific immunoglobulins that can not be differentiated from the specific immunoglobulins.

Another method of detecting bound antibodies involves combining the sample and a competing labeled antibody, with a support-bound antigen, Schuurs, et al., U.S. Pat. No. 3,654,090. This method has its limitations because antibodies in sera will bind numerous epitopes, making competition inefficient.

For detection of bound antigen, the antigen can be used in excess of the maximum amount of antibody that is present in the sample or in an amount that is less than the amount of antibody. For example, radioimmunoprecipitation ("RIP") assays for GAD autoantibodies have been developed and are currently in use, Atkinson, et al., *Lancet* 335:1357–1360 (1990). However, attempts to convert this assay to an enzyme linked immunosorbent assay ("ELISA") format have not been successful. The RIP assay is based on precipitation of immunoglobulins in human sera, and led to the development of a radioimmunoassay ("RIA") for GAD autoantibodies. In both the RIP and the RIA, the antigen is added in excess and the bound antigen:antibody complex is precipitated with protein A-Sepharose. The complex is then washed or further separated by electrophoresis and the antigen in the complex is detected.

Other precipitating agents can be used such as rheumatoid factor or C1q, Masson, et al., U.S. Pat. No. 4,062,935; polyethylene glycol, Soeldner, et al., U.S. Pat. No. 4,855, 242; and protein A, Ito, et al., EP 0,410,893 A2. The precipitated antigen can be measured to indicate the amount of antibody in the sample; the amount of antigen remaining in solution can be measured; or both the precipitated antigen and the soluble antigen can be measured to correct for any labeled antigen that is non-specifically precipitated. These methods, while quite sensitive, are all difficult to carry out because of the need for rigorous separation of the free antigen from the bound complex, which requires at a minimum filtration or centrifugation and multiple washing of the precipitate.

Alternatively, detection of the bound antigen can be employed when the amount of antigen is less than the maximum amount of antibody. Normally, that is carried out using particles such as latex particles or erythrocytes that are coated with the antigen, Cambiaso, et al., U.S. Pat. No. 4,184,849 and Uchida, et al., EP 0,070,527 A1. Antibodies can specifically agglutinate these particles and can then be detected by light scattering or other methods. It is necessary in these assays to use a precise amount of antigen as too little antigen provides an assay response that is biphasic and high antibody titers can be read as negative, while too much antigen adversely affects the sensitivity. It is therefore necessary to carry out sequential dilutions of the sample to assure that positive samples are not missed. Further, these assays tend to detect only antibodies with relatively high affinities and the sensitivity of the method is compromised by the tendency for all of the binding sites of each antibody to bind to the antigen on the particle to which it first binds, leaving no sites for binding to the other particle.

For assays in which the free antigen is detected, the antigen might also be added in excess or in a limited amount although only the former has been reported. Assays of this type have been described where an excess of antigen is added to the sample, the immunoglobulins are precipitated, and the antigen remaining in the solution is measured, Masson, et al., supra and Soeldner, et al., supra. These assays are relatively insensitive because only a small percentage change in the amount of free antigen occurs with low amounts of antibody, and this small percentage is difficult to measure accurately.

Practical assays in which the free antigen is detected and the antigen is not present in excess of the maximum amount of antibody expected in a sample have not been described. However, in van Erp, et al., *Journal of Immunoassay* 12(3):425–443 (1991), a fixed concentration of monoclonal antibody was incubated with a concentration dilution series of antigen, and free antigen was then measured using a gold sol particle agglutination immunoassay to determine antibody affinity constants.

There has been much research in the area of evaluating useful markers for determining the risk factor for patients developing IDDM. These include insulin autoantibodies, Soeldner, et al., supra and circulating autoantibodies to glutamic acid decarboxylase ("GAD"), Atkinson, et al., PCT/US89/05570 and Tobin, et al., PCT/US91/06872. In addition, Rabin, et al., U.S. Pat. No. 5,200,318 describes numerous assay formats for the detection of GAD and pancreatic islet cell antigen autoantibodies. GAD autoantibodies are of particular diagnostic importance because they occur in preclinical stages of the disease, which may make therapeutic intervention possible. However, the use of GAD autoantibodies as a diagnostic marker has been impeded by the lack of a convenient, nonisotopic assay.

One assay method involves incubating a support-bound antigen with the sample, then adding a labeled anti-human immunoglobulin. This is the basis for numerous commercially available assay kits for antibodies such as the Syn$^{elisa}$ kit which assays for autoantibodies to $GAD_{65}$, and is described in product literature entitled "Syn$^{elisa}$ GAD II-Antibodies" (Elias USA, Inc.). Substantial dilution of the sample is required because the method is subject to high background signals from adsorption of non-specific human immunoglobulins to the support.

Many of the assays described above involve detection of antibody that becomes bound to an immobilized antigen. This can have an adverse affect on the sensitivity of the assay due to difficulty in distinguishing between specific immunoglobulins and other immunoglobulins in the sample, which bind non-specifically to the immobilized antigen. There is not only a need to develop an assay that avoids non-specific detection of immunoglobulins, but there is also the need for an improved method of detecting antibodies that combines the sensitivity advantage of immunoprecipitation assays with a simplified protocol. Finally, assays that can help evaluate the risk of developing diseases such as IDDM are medically and economically very important. The present invention addresses these needs.

SUMMARY OF THE INVENTION

The present invention pertains to methods of determining the presence or amount of antibodies in a sample suspected of containing the antibodies.

One aspect of the invention pertains to combining the sample with an antigen that binds the antibodies in the sample to form an antigen:antibody complex. The amount of antigen employed is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample.

Another aspect of the invention relates to the use of a first binding agent that binds the complex and does not bind the antigen when the antigen is not part of the complex, and to the use of a second binding agent that selectively binds the antigen relative to binding the complex when the complex is bound to the first binding agent. The first binding agent can be bound to a soluble polymer or suspendable solid phase. The second binding agent can be bound to a solid phase. The second binding agent can also be two receptors that bind the antigen, where each receptor is bound to a signal producing system member.

Another aspect of the invention relates to detecting the presence or amount of antigen that is not part of the complex, as an indicator of the presence or amount of the antibodies in the sample.

The present invention also pertains to a method of determining the presence or amount of glutamic acid decarboxylase ("GAD") autoantibodies.

Another aspect of the invention is an improvement for an assay wherein a sample suspected of containing a target antibody and an antigen that binds the antibody are combined to form a mixture containing an antigen:antibody complex and free antigen, and the free antigen is detected. The improvement involves using an amount of antigen that is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample. In another aspect of the invention, the improvement involves adding a first binding agent that binds the complex but does not bind free antigen, followed by the addition of a second binding agent that binds free antigen but does not bind antigen when it is part of the first agent-bound complex.

The present invention also relates to kits for use in these methods.

DESCRIPTION OF THE SPECIFIC EMBODIMENTS

Before proceeding further with the description of the specific embodiments of the present invention, a number of terms will be defined.

Analyte: The antibodies or autoantibodies to be detected. These include complete immunoglobulins or fragments thereof, and include the various classes and isotypes, such as IgA, IgD, IgE, IgG1, IgG2a, IgG2b and IgG3 and IgM.

Antigen: A compound against which antibodies can be raised, and which is capable of binding to an antibody to form specific antibody:antigen complexes. The antigen is bound by the antibody analyte, usually a biomolecule, mammalian, viral or microbiological in origin or a mimic thereof, or other molecules of synthetic or natural origin that are in the environment such as drugs, pesticides, environmental contaminants and the like. The antigen may be used in the assay in its natural form or it may be modified provided the modification does not interfere with its antigenicity. Typical modifications include binding covalently or non-covalently to the antigen, a specific binding pair member and/or a detectable label, either or both of which can facilitate detection of the antigen.

Sample suspected of containing the analyte: any sample which is reasonably suspected of containing the antibodies or autoantibodies of interest, can be analyzed by the methods of the present invention. The sample is typically an aqueous solution such as a body fluid from a host, for example, urine, whole blood, plasma, serum, saliva, semen, stool, sputum, cerebral spinal fluid, tears, mucus, or the like, but preferably is plasma or serum. The sample can be pretreated as described below and can be prepared in any convenient medium which does not interfere with the assay. An aqueous medium is preferred.

Member of a specific binding pair ("sbp" member): one of two different molecules having an area on the surface or in a cavity that specifically binds to and is therefore defined as complementary with a particular spatial and polar organization of the other molecule. The sbp members can be referred to as ligand and receptor such as members of an immunological pair, e.g., antigen-antibody. As used herein, the term "ligand" refers to any organic compound for which a receptor naturally exists or can be prepared and the term "receptor" refers to any compound or composition capable of recognizing a particular spatial and polar organization of a molecule, i.e., epitopic or determinant site. Complementary sbp members bind to one another, as for example, a ligand and its complementary receptor. Sbp members can be immunological pairs such as antigen and antibody, or non-immunological pairs such as avidin and biotin or the complementary strands of an oligonucleotide. Sbp members can also be small molecules or residues of small molecules and their receptors. Small molecules have a molecular weight of from 100–2000, preferably 150–1000, and a receptor for the small molecule either exists or can be prepared. Examples of small molecules include derivatives of biotin, lysergic acid, fluorescein or a fluorescein derivative, and vitamin $B_{12}$, with the corresponding receptors being avidin or streptavidin, anti-lysergic acid, anti-fluorescein and intrinsic factor, respectively. Small molecules are often covalently bound to other sbp members to form a conjugate having at least one, and frequently 2–20, small molecules. Bonding of the small molecule to the sbp member may be accomplished by chemical reactions which result in replacing a hydrogen atom of the small molecule with a bond to the sbp member or by a linking group between the small molecule and the sbp member of any size but preferably no larger than necessary to permit binding to the conjugate of both a receptor for the small molecule and the sbp member. Antibodies to small molecules can be prepared by immunizing animals with an immunogen prepared by linking the small molecule to an immunogenic carrier.

Support or surface: The solid phase is typically a support or surface, which is a porous or non-porous water insoluble material that can have any one of a number of shapes, such as strip, rod, particle, including beads and the like. Suitable materials are well known in the art and are described in, for example, Ullman, et al. U.S. Pat. No. 5,185,243, columns 10–11, Kurn, et al., U.S. Pat. No. 4,868,104, column 6, lines 21–42 and Milburn, et al., U.S. Pat. No. 4,959,303, column 6, lines 14–31 which are incorporated herein by reference. Binding of ligands and receptors to the support or surface may be accomplished by well-known techniques, readily available in the literature. See, for example, "Immobilized Enzymes," Ichiro Chibata, Halsted Press, New York (1978) and Cuatrecasas, *J. Biol. Chem.* 245:3059 (1970). Whatever type of solid support is used, it must be treated so as to have bound to its surface either a receptor or ligand that directly or indirectly binds the antigen. Typical receptors include antibodies, intrinsic factor, specifically reactive chemical agents such as sulfhydryl groups that can react with a group on the antigen, and the like. For example, avidin or streptavidin can be covalently bound to spherical glass beads of 0.5–1.5 mm and used to capture a biotinylated antigen.

Signal producing system ("sps"): one or more components, at least one component being a label, which generate a detectable signal that relates to the amount of bound and/or unbound label, i.e. the amount of label bound or not bound to the compound being detected. The label is any molecule that produces or can be induced to produce a signal, such as a fluorescer, enzyme, chemiluminescer or photosensitizer. Thus, the signal is detected and/or measured by detecting enzyme activity, luminescence or light absorbance.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as Qβ replicase; promoters; dyes; fluorescers such as fluorescein isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; photosensitizers; particles such as latex or carbon particles; suspendable particles; metal sol; crystallite; liposomes; cells, etc., which may be further labeled with a dye, catalyst or other detectable group.

Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference. Preferably, at least one sps member is selected from the group consisting of fluorescers, enzymes, chemiluminescers, photosensitizers and suspendable particles.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the sps would then include all the components required to produce a measurable signal, which may include substrates, coenzymes, enhancers, additional enzymes, substances that react with enzymic products, catalysts, activators, cofactors, inhibitors, scavengers, metal ions, specific binding substance required for binding of signal generating substances, and the like. A detailed discussion of suitable signal producing systems can be found in Ullman, et al. U.S. Pat. No. 5,185,243, columns 11–13, which is incorporated herein by reference.

The label is bound to an sbp member which is the antigen, or is capable of directly or indirectly binding the antigen, or is a receptor for the antigen, and includes, without limitation, the antigen; a ligand for a receptor bound to the antigen; a receptor for a ligand bound to the antigen; an antibody that binds the antigen; a receptor for an antibody that binds the antigen; a receptor for a molecule conjugated to an antibody to the antigen; an antigen surrogate capable of binding a receptor for the antigen; a ligand that binds the antigen, etc. Bonding of the label to the sbp member may be accomplished by means of non-covalent bonding as for example by formation of a complex of the label with an antibody to the label or by means of covalent bonding as for example by chemical reactions which result in replacing a hydrogen atom of the label with a bond to the sbp member or may include a linking group between the label and the sbp member. Such methods of conjugation are well known in the art. See for example, Rubenstein, et al., U.S. Pat. No. 3,817,837, which is incorporated herein by reference. Other sps members may also be bound covalently to sbp members. For example, in Ullman, et al., U.S. Pat. No. 3,996,345, two sps members such as a fluorescer and quencher can be bound respectively to two sbp members that both bind the analyte, thus forming a fluorescer-$sbp_1$:analyte:$sbp_2$-quencher complex. Formation of the complex brings the fluorescer and quencher in close proximity, thus permitting the quencher to interact with the fluorescer to produce a signal. This is a fluorescent excitation transfer immunoassay. Another concept is described in Ullman, et al., EP 0,515,194 A2, which uses a chemiluminescent compound and a photosensitizer as the sps members. This is referred to as a luminescent Oxygen channeling immunoassay. Both the aforementioned references are incorporated herein by reference.

Ancillary Materials: Various ancillary materials will frequently be employed in the methods in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, or surfactants, particularly non-ionic surfactants, binding enhancers, e.g., polyalkylene glycols, or the like.

As mentioned above, the present invention pertains to methods to detect the presence or amount antibodies, preferably serum antibodies, in a sample suspected of containing the antibodies. The methods combine the sensitivity advantage of immunoprecipitation assays with a simplified protocol.

The methods of this invention afford several important advantages over previous ELISA methods of detecting antibodies. "Traditional" ELISA methods of detecting antibodies involve binding antibodies in a sample to an antigen, separating the resulting antigen:antibody complex from the sample and then detecting the antibodies or the antigen. When an antibody binds directly to an immobilized antigen, the antibody is detected, but sensitive detection of this antigen-bound specific immunoglobulin is difficult because of non-specific binding of irrelevant immunoglobulins in the sample, which may be present in large amounts. As a result, assays that directly measure the amount of bound antibodies often have limited sensitivity. An additional complication arises when assaying for autoantibodies because some patients may have very low titers of the autoantibodies being detected. The present invention does not detect antibodies directly and is therefore not affected by non-specific binding of immunoglobulins. Furthermore, when immune complexes are analyzed for antigen, tedious separation and washing steps are required during which there is a risk that some of the antigen will be lost. The present method avoids this step. Since antigen detection can be carried out by a homogeneous method very simple protocols can be used since no separation steps are required for the entire process in accordance with the present invention.

A key aspect of the present invention is the molar amount of antigen that is added to the medium containing the sample, which is usually less than 1µM, frequently less than 1 nM, and preferably less than 0.1 nM and is added in an amount not to exceed the highest expected amount of antibodies in the sample. Measurement of free antigen remaining after binding to the antibodies permits exceptionally sensitive detection of the antibodies. Although high concentrations of the antibodies cannot be quantitated, there is no risk of missing high titer samples as occurs in direct latex agglutination assays. Were a large excess of antigen to be added, i.e., if the molar amount of antigen were greater than the highest expected molar amount of antibody, such as in a typical RIP assay, there is a loss of sensitivity due to the inability to obtain an accurate measurement of the reduction in free antigen with low titer samples.

Maximum sensitivity therefore requires the use of a low concentration of the antigen. Although, the lowest practical concentration of the antigen will be the lowest concentration that can be detected if the sample has no antibody, it will normally be desirable to use up to 1000 times this minimum detectible concentration, preferably no more than 100 times the minimum detectible concentration. In general, the more antigen that is used, the larger the range of antibody concentrations that can be accurately measured and the lower the sensitivity of the assay.

The minimum amount of antigen that is added in the methods of the present invention is determined by the detection limit of the antigen in the absence of antibody in the sample, i.e,. enough antigen has to be added so that it is detectable by the assay method being used. This value is readily ascertainable by one skilled in the art by running a series of tests, starting with zero antigen and using incremental known amounts of antigen until a level of antigen is achieved that can be reliably detected by the method used in the assay. As used herein, the term "reliably" means that the same assay can be performed repeatedly and the antigen will be reproducibly detected. The minimum amount of antigen that can be reliably detected is defined as the amount of antigen that will provide a signal that will differ by about three standard deviations from the signal obtained when no antigen is present. For example, when the method to be used in the assay is ELISA, anti-antigen antibodies are bound to a support and samples of varying known amounts of antigen are added to the support. The support is washed, enzyme labeled antibodies are added to the support, which is washed again, followed by the addition of enzyme substrate. The rate of conversion of the substrate to product is related to the amount of antigen present. When a level of antigen is reached that can be detected repeatedly over several assay runs, that amount is referred to as "the minimum amount of antigen that can be reliably detected when there are no antibodies present in a sample".

The maximum amount of antigen to be added to an assay will not exceed the highest expected amount of antibody that will be introduced into the assay from the sample and will usually be at least 100 fold lower than the highest expected amount of antibody. For this purpose an accurate measure of the amount of antibody in a sample can be obtained by carrying out an assay of the present invention using an arbitrarily fixed concentration of the antigen and repeating the assay on sequential dilutions of the sample. The amount of antibodies in the sample is taken as two times the amount of antigen divided by the dilution factor when the signal due to free antigen in the assay is reduced by 50% due to added sample.

The amount of antigen added to the medium in the present invention can also be expressed as "Z", where Z is within the range of X to nX and Z is less than Y. The value "n" is within the range of 5–1000, preferably 10–100. The amount "X" is the minimum amount of antigen that can be reliably detected when there are no antibodies present in a sample and the amount "Y" is the maximum expected amount of antibodies in the sample.

One embodiment of this aspect of the invention is a method comprising the steps of: (a) bringing together in an aqueous medium to form a mixture: (i) the sample suspected of containing specific antibodies to an antigen, (ii) an antigen that binds the antibodies to form an antigen: antibody complex, wherein the amount of antigen added to the medium is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample, and (iii) a first binding agent that binds the complex and does not bind the antigen when the antigen is not part of the complex; (b) adding to the mixture a second binding agent that selectively binds the antigen relative to binding the complex when the complex is bound to the first binding agent; and (c) detecting the antigen bound to the second binding agent, the presence or amount thereof being related to the presence or amount of the antibodies in the sample.

As used herein the term "antigen:antibody complex" means the complex formed by the immunological binding of an antigen to an antibody. As used herein, the term "selectively binds" means that the second binding agent has the ability to bind preferentially to the free antigen relative to binding the antigen:antibody complex when the complex is bound to the first binding agent. Free antigen is antigen in the mixture that has not formed a complex with the antibody analyte. The affinity of the second binding agent for the free antigen will be at least 5-fold and preferably at least 10-fold its affinity for the first binding agent-bound complex. This preferential binding can be kinetic or thermodynamic and will usually be a result of charge repulsion and/or steric hindrance. For example, the first binding agent, when bound to the antigen:antibody complex, may be of such bulk that the second binding agent is unable to bind any antigen present in the complex to any significant degree. Therefore, only free antigen will become bound to the second binding agent.

A critical feature of the present invention is that the first binding agent can bind the antigen:antibody complex in a manner that precludes binding of the second binding agent to the complex. The binding agents are sbp members and binding of the second binding agent to the first binding agent-bound complex can be better prevented when the first binding agent is bound to a soluble polymer or suspendable solid phase. This provides the added advantage that the first binding agent-bound complex does not need to be separated from the medium prior to the addition of the second binding agent because the first binding agent-bound complex does not interfere with the measurement of free antigen.

The sbp member that makes up the first binding agent is selected so that it binds the antigen:antibody complex and does not bind the antigen when the antigen is not part of the complex, i.e., the first binding agent does not significantly bind to any free or unbound antigen present in the medium. The sbp member may also bind other substances present in the sample, e.g., non-analyte antibodies. This is acceptable provided that the first binding agent does not bind antigen except when the antigen is bound to the analyte antibody.

Suitable sbp members for the first binding agents include, without limitation, antibodies to immunoglobulins; complement factor, C1q; rheumatoid factor; protein G and/or protein A. Some of these materials non-selectively bind certain immunoglobulins, for example, antibodies and protein A, and some selectively bind immune complexes, for example, C1q and rheumatoid factor. As noted above, in order to prevent binding of the second binding agent to the antigen:antibody complex, it is preferable, although not necessary, to have the first binding agent further comprised of a suspendable solid phase or soluble polymer, i.e, the binding agent is bound to a suspendable solid phase or soluble polymer.

Suitable soluble polymers are linear or preferably branched and include, by way of illustration and not limitation, polysaccharides such as dextran and heparin; polyacrylates, polyacryloyl glucosamine, polyvinyl-pyrrolidone and the like. The polymers will usually have a molecular weight of at least 10,000 and preferably, the soluble polymers comprising the first binding agent have molecular weights of over 250,000.

Suitable suspendable solid phases include, by way of illustration and not limitation, latex, glass particles, particularly porous glass particles, polyacrylamide particles, agarose, SEPHADEX® (Pharmacia Fine Chemicals, Inc.), as well as other particulate phases that are not strictly solids such as liposomes, oil droplets and so forth. Numerous of the aforementioned soluble polymers can be cross-liked to provide suspendable solid phase materials. These materials will usually be particulate and will range in size from 10 nm to 100 nm, preferably from 100 nm to 10 nm.

The second binding agent is an sbp member that is capable of binding the antigen. It can be an antibody, preferably a monoclonal antibody, or other receptor for the antigen; a ligand to which the antigen binds as for example an irreversible inhibitor if the antigen is an enzyme; or one member of an sbp where the other member is bound to the antigen. For example, biotin can be conjugated to the antigen, and the sbp member comprising the second binding agent can be avidin, streptavidin, or antibodies to biotin. Alternating the second binding agent can be a chemically reactive group that reacts specifically with groups on the antigen. For example, the second binding agent could have bromoacetamide groups that can bind specifically with sulfhydryl groups on the antigen.

The second binding agent can be bound to a soluble polymer or a suspendable or non-suspendable solid phase any of which may further comprise a label to permit detection of antigen bound to the second binding agent. The soluble polymers and suspendable supports will preferably comprise a label and include polymers such as nucleic acids, proteins, dextrans and polyacrylates; aggregates such as immune complexes particles such as latex agarose SEPHADEX® dye crystallites, liposomes, oil droplets, metal sols, and the like. The non-suspendable solid phases include bibulous materials such as glass or cellulose paper; plastics such as polystyrene, nylon, polymethacrylate, etc.; silicons, metals such as gold and indium, and the like.

After addition of the second binding agent, the antigen bound to the second binding agent is detected, its presence or amount being related to the presence or amount of the antibodies in the sample. This relationship is inversely proportional since the higher the concentration of antibodies present in the sample, the lower the amount of free antigen, i.e., the amount of antigen that becomes bound to the second binding agent.

Detection of the free antigen can be accomplished in numerous ways. In heterogeneous formats, the second binding agent is bound to a separable support, i.e., a suspendable or non-suspendable solid phase. For example, the second binding agent can be an anti-antigen antibody or a receptor such as streptavidin that can bind to a ligand that is bound to the antigen. In these formats the sample and the antigen are first combined and the first binding agent is then added. After addition of the second binding reagent bound to a support, the support is separated from the mixture. The amount of antigen that has become bound to the second binding agent-support can be measured directly or indirectly. When the antigen has a label bound to it, the presence of the label on the support can be detected. With certain supports, particularly indium, silica, and acoustic devices, even unlabeled antigen can be directly measured. Alternatively, the antigen can be indirectly measured by adding a reagent that will cause the antigen to be specifically labeled, e.g., by adding a labeling agent such as a labeled antibody to the antigen. The label can then be detected by methods well known to those skilled in the art.

In the aforementioned heterogeneous formats the solid phase provides a means for efficient separation of the assay mixture or labeling agents from the surface bound antigen. Typically the separable support will comprise a surface such as the surface of a microtiter well, a porous material such as paper or nitrocellulose, or beads such as magnetizable particles. The antigen, bound to the solid phase can then be detected. The antigen can be bound to or capable of being bound to an sps member. For example, the antigen can be bound to an enzyme such as horseradish peroxidase or can be contacted with a receptor bound to an sps member such as an enzyme-labeled anti-antigen antibody. Alternately, where the antigen has an sbp member bound to it, the second binding agent-solid phase to which the antigen has become bound, can contacted with a labeled complementary sbp member. After incubation of the support-bound antigen with the complimentary sbp member, the support is usually separated from the complementary sbp member and the presence of label on the support is detected.

In homogeneous formats, it is not necessary to separate the antigen bound to the second binding agent to cause it to be detectible. For example, the second binding agent could be immobilized on an acoustic coupled device as the solid phase or on a solid phase that provides for surface plasmon resonance or evanescent wave fluorescence detection, none of which require separation of the liquid phase to detect antigen bound to the surface. Alternatively, the signal from a label bound to the antigen could be modulated by the solid phase or by a polymer or other aggregate or suspendable solid phase bound to the second binding agent. For this purpose the label could be, for example, a sensitizer, fluorescer, enzyme or quencher whereupon the second binding agent would be bound directly or indirectly to a chemiluminescent particle, a quencher, a second enzyme, or a fluorescer, respectively. Binding between the two members of each of these pairs permits direct detection of binding by, for example, the techniques used in the luminescent oxygen channeling immunoassay and the fluorescent excitation transfer immunoassay.

Another embodiment of this aspect of the invention is a method comprising the steps of: (a) bringing together in an aqueous medium: (i) the sample suspected of containing the antibodies against a certain antigen, (ii) an antigen that binds the antibodies to forman antigen:antibody complex, wherein the amount of antigen added to the medium is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample, and (iii) a first binding agent that binds the complex and does not bind the antigen when the antigen is not part of the complex; (b) contacting the medium with a second binding agent bound to a solid phase, wherein the second binding agent is a receptor that binds the antigen to form solid phase-bound antigen but does not bind the antigen:antibody complex; (c) detecting the antigen bound to the solid phase, the presence or amount thereof being related to the presence or amount of the antibodies in the sample.

This embodiment is illustrated by the following example. A serum sample suspected of containing antibodies ("Ab") against a hepatitis A virus antigen ("$Ag_{HAV}$") is incubated for one hour in an aqueous medium with $Ag_{HAV}$ bound to a fluorescent label. The $Ag_{HAV}$ binds the antibodies to form an $Ag_{HAV}$:Ab complex. The amount of $Ag_{HAV}$ added to the medium is 100 times the minimum amount of $Ag_{HAV}$ that can be reliably detected when there are no antibodies present in a sample and is over 1000 times lower on a molar basis that the highest amount of $Ag_{HAV}$ antibodies found in a clinical sample. Anti-human immunoglobulin antibodies bound to 250,000 molecular weight dextran are added. The anti-human immunoglobulin antibodies bind the $Ag_{HAV}$:Ab complex but do not bind any $Ag_{HAV}$ that is not part of the complex. After an additional one hour incubation, the medium is added to a microtiter well to which is bound monoclonal anti-$Ag_{HAV}$ antibodies that bind the $Ag_{HAV}$, to form support-bound $Ag_{HAV}$. These antibodies do not bind the $Ag_{HAV}$:Ab complex. After a third one hour incubation, the support-bound $Ag_{HAV}$ is detected by thoroughly washing the well and measuring the residual fluorescence, the amount thereof being inversely related to the amount of the antibodies in the sample.

An alternative method of detecting the antigen involves contacting the solid phase with a labeled sbp member, which binds the solid phase-bound antigen. After incubation, the excess sbp member is washed away and any sps members in addition to the label that are needed to produce a signal are added. The signal is then measured, the amount thereof being inversely related to the amount of the antibodies in the sample. For example, an enzyme labeled second monoclonal anti-$Ag_{HAV}$ antibody can be added, followed after washing by the addition of substrate.

Yet another embodiment of this aspect of the invention comprises the steps of (a) bringing together in an aqueous medium: (i) the sample suspected of containing the antibodies, (ii) an antigen that binds the antibodies to form an antigen:antibody complex, wherein the amount of antigen added to the medium is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample, and (iii) a first binding agent that binds the complex and does not bind the antigen when the antigen is not part of the complex; (b) adding to the medium a second binding agent comprised of two receptors that bind the antigen, where at least one of the receptors is unable to bind effectively to the complex when the complex is bound to the binding agent; and (c) detecting the complex formed when the receptors bind the antigen.

This embodiment can be used to detect numerous antibodies such as those present in a patient who has the human immunodeficiency virus ("HIV"), rubella or herpes. The following example illustrates an assay of the present invention for detecting antibodies against HIV. A sample suspected of containing antibodies against HIV is brought together in an aqueous medium with the HIV antigen ("$Ag_{HIV}$"), which binds the antibodies to forman $Ag_{HIV}$:Ab complex. As with above, the amount of $Ag_{HIV}$ added is Z, which is within the range of X to nX and is less than Y, where n is 100, X is the minimum amount of $Ag_{HIV}$ that can be reliably detected when there are no antibodies present in a sample and Y is the maximum expected amount of antibodies in the sample. After incubation for one hour, goat antibodies to human immunoglobulins bound to dextran sulfate are added. The first binding agent binds the $Ag_{HIV}$:Ab complex but does not bind $Ag_{HIV}$ when it is not part of the complex. After incubation, two receptors for the $Ag_{HIV}$ are added to the medium. At least one, and preferably two of the receptors, are bound to latex particles which serve to prevent binding of the receptors to the $Ag_{HIV}$:Ab complex bound to the dextran sulfate. Conveniently, the two receptors are non-competing monoclonal antibodies to $Ag_{HIV}$. One of the antibodies can be bound to particles in which a chemiluminescer is dissolved, such as N-methylbenzalacridan. The other antibody can be bound directly to a sensitizer or preferably to latex particles in which a sensitizer is dissolved such as chlorophyll A. At least the former of these antibodies is unable to bind effectively to the $Ag_{HIV}$:Ab complex when the complex is bound to the first binding agent. The chemiluminescer-$Ab_1$:$Ag_{HIV}$:$Ab_2$-sensitizer complex is detected after a 10 minute incubation by a one minute irradiation with light having wavelengths in excess of 600 nm and measuring the delayed luminescence at 400–500 nm, following termination of irradiation.

This invention finds particular utility in detecting autoantibodies to insulin; to glutamic acid decarboxylase ("GAD"), both the 65 kd and the 67 kd isoforms but more particularly, $GAD_{65}$; and to islet cell antigens. One method of determining the presence or amount of GAD autoantibodies in a sample suspected of containing the autoantibodies, comprises the steps of bringing together in an aqueous medium: (i) the sample, (ii) GAD antigen that binds the autoantibodies to forman antigen:autoantibody complex, wherein the amount of antigen added to the medium is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample, (iii) a first binding agent that, wherein the first binding agent is a receptor for the autoantibodies that binds the complex, and is bound to a material selected from the group consisting of a suspendable solid phase and a soluble polymer; adding to the medium a second binding agent that selectively binds the antigen relative to binding the complex when the complex is not separated from the medium; and detecting the binding of the second binding agent to the antigen, the binding thereof being related to the presence or amount of the autoantibodies in the sample.

The GAD protein can be obtained by isolation and purification from a biological source, preferably mammalian such as rat, feline or porcine. Particularly good results have been obtained by using porcine brain GAD. In addition, the DNA sequence of GAD is known and can be used to recombinantly produce GAD. Rabin, et al., supra, at column 4, line 51 to column 5, line 32, describes numerous sources and techniques for obtaining both isoforms of GAD, the disclosure of which is incorporated herein by reference.

The preferable amount of GAD antigen, "Z", is 0.01–12.0 fmol, more preferably 0.025–7.5 fmol, and even more preferably, the amount of GAD antigen is 0.1–2.0 fmole. This "Z" value was determined from the "X" value in experiments such as that described in Example V and the "Y" value, which is up to $10^{-8}M$.

The above method is illustrated by the following example. Recombinant $GAD_{65}$ is labeled with biotin to provide bGAD. This conjugate is then incubated with patient serum samples. A suspension of Sepharose coupled to protein-A is then added and the incubation continued. The suspension is transferred to a microtiter well that has been coated with streptavidin. After incubation to bind free bGAD, the well is washed and incubated with a mouse monoclonal antibody to GAD, which is either conjugated to a label such as horseradish peroxidase ("HRP") or unconjugated. When unconjugated antibodies are used, the well is washed again and then incubated with labeled anti-mouse IgG antibodies. In either case, after the labeled antibodies are added, the well is washed a final time and incubated with any additional sps members. For example, if the label is HRP, then the final incubation could include a solution containing hydrogen peroxide and tetramethylbenzidine, and color development would be read after incubation.

In an assay performed following this format in the present invention, samples that were known to be anti-$GAD_{65}$ negative showed minimal suppression in signal. Samples that were known to be anti-$GAD_{65}$ positive had suppressed color development.

This aspect of the invention is illustrated in an assay for determining the presence or amount of antibodies in a sample suspected of containing the antibodies for use in the detection or monitoring of a human disease. For example, the assay for $GAD_{65}$ autoantibodies is useful in the detection of IDDM.

Another embodiment comprises an improved assay comprising combining in an aqueous medium the sample and an antigen that binds the antibodies to form a mixture comprised of an antigen:antibody complex and free antigen; and detecting the free antigen, the presence or amount thereof being related to the presence or amount of the antibodies in the sample. In one embodiment, the improvement comprises using an amount of antigen that is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample. In another embodiment, the improvement comprises adding a first binding agent that binds the complex but does not bind the antigen, followed by the addition of a second binding agent that binds free antigen but does not bind antigen when it is part of the complex.

Antibodies useful in the methods of the present invention can be monoclonal or polyclonal and can be prepared by techniques that are well known in the art such as immunization of a host and collection of sera from which the immunoglobulin can be separated by known techniques (polyclonal), by preparing continuous hybrid cell lines and collecting the secreted protein (monoclonal) as described by Milsrein and Kohler in *Nature* 256:495–7 (1975), or by cloning and expressing nucleotide sequences or mutagenized versions thereof coding at least for the amino acid sequences required for specific binding of natural antibodies. Antibodies may include the complete immunoglobulin or a fragment thereof, and include the various classes and isotypes, such as IgA, IgD, IgE, IgG1, IgG2a, IgG2b and IgG3 and IgM. Fragments may include Fab, Fv, F(ab')2 and Fab.

Appropriate reaction conditions are chosen for carrying out the methods in accordance with the present invention. The following description sets forth suitable conditions, which are subject to modification by those skilled in the art depending on the specific reagents and assay protocol chosen for any particular application. For example, the methods of this invention can be applied to numerous types of assays such as heterogeneous or homogeneous, and the conditions and reagents used will be selected accordingly.

The sample, preferably in a suitable medium, can be examined directly or may be pretreated before the sample is added to the assay medium. Pretreatment can render the antibody analyte more readily available to one or more of the assay reagents or more readily detectable by reducing interference in the assay by removing any unwanted materials. The sample may be pretreated to separate or lyse cells; precipitate, hydrolyse or denature proteins; hydrolyze lipids; or the like. Such pretreatment may include, without limitation: centrifugation; treatment of the sample with an organic solvent, for example, an alcohol, preferably an alcohol having less than about 7 carbon atoms such as methanol; and treatment with detergents.

The concentration of the antibodies to be assayed will generally vary from about 0 to $10^{-5}M$, more usually from about 0 to $10^{-8}M$. The relative amounts of the various reagents used in the assay and packaged in the kits described below, can be varied widely to provide for concentrations of the reagents that substantially optimize the reactions that need to occur during the present method and to further substantially optimize the sensitivity of any assay performed. For example, considerations such as the tradeoff between sensitivity and the assay range, the particular detection technique, and the concentration of the analyte will determine the concentration of antigen used, as explained above, and will normally determine the concentration of the other reagents also. In addition, the final concentration of each of the reagents will normally be determined empirically to optimize the sensitivity of the assay over the range of interest. Since the unbound or "free" antigen is what is being measured, a variation in concentration of antigen which is of significance should provide an accurately measurable signal difference.

In carrying out the method of this invention, preferably an aqueous buffered medium at a moderate pH will be employed, generally that which provides optimum assay sensitivity. The aqueous medium may be solely water or may include a cosolvent such as an oxygenated organic solvent of from 1–6, more usually from 1–4 carbon atoms, including alcohols, ethers and the like. Usually the cosolvent will be present in less than about 70 weight percent, more usually, in less than about 30 weight percent.

In assays in accordance with the present invention, the pH for the medium will usually be in the range of about 5–10, preferably, in the range of about 7–9. The pH is chosen so as to maintain a significant level of binding between sbp members, while optimizing signal producing proficiency. In some instances, a compromise will be made between these two considerations.

Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the method and usually constant temperatures during the period of the measurement, particularly for rate determinations. The temperature may vary with the step being undertaken, with the temperatures ranging from 5°–50° C., usually from about 15°–40° C. Incubation temperatures will normally range from 5°–45° C., more usually from 15°–40° C. Temperatures during measurements will generally range from 10°–50°C., more usually from 15°–40°C.

While the order of addition of the various reagents is limited, numerous protocols can be devised by using various techniques for timed release of reagents. Where such procedures are not employed, it will usually be preferable to combine the sample and antigen before or nearly simultaneously with the first binding agent. Where the first binding agent can bind the antigen:antibody complex without binding the uncomplexed immunoglobulins, the order of addition of these reagents is unimportant. Addition of the second binding agent must be subsequent to the first two additions unless a means is provided for the timed release of this agent. Other reagents capable of binding the antigen can be added at any time but are preferably added nearly simultaneously with or subsequent to addition of the second binding agent. The timing of the addition of other reagents may vary widely.

Optionally, one or more incubation steps may be involved after each reagent addition, generally ranging from. about 30 seconds to 6 hours, more usually from about 2 minutes to 1 hour. In addition, the assay may involve one or more wash steps, as needed.

The final step of an immunoassay is to measure the amount of free antigen, which is related to the presence or amount of the antibody analyte in the sample. There are numerous ways to measure free antigen which are well known in the art. For example, the antigen can be conjugated to a detectable label, or can be contacted with a detectably labeled anti-antigen antibody. The signal produced is related to the amount of antigen present, which is inversely related to the amount of antibodies in the sample.

For illustrative purposes, the following assay protocols can be utilized. These illustrations should not be construed as limiting the scope of the invention, but are merely illustrative of the qualitative, semi-quantitative and quantitative assay protocols in which the method of this invention can be used for determining the presence or amount of antibodies in a sample. The signal detected in these methods is compared to a standard or control, having a known concentration of antibodies.

(A) In an assay for insulin autoantibodies, a sample suspected of containing the antibodies is combined with insulin in a suitable medium. Complement factor ("C1q") bound to agarose is added and the mixture is incubated. A monoclonal anti-insulin antibody bound to 2,000,000 molecular weight dextran and labeled with a quencher such as rhodamine B is added. After incubation, the agarose is allowed to settle and the aqueous medium is combined with a second non-competing monoclonal anti-insulin antibody labeled with a fluorescer such as fluorescein. The amount of quenching of the fluorescer is then related to the amount of insulin present, which is inversely proportional to the amount of insulin autoantibodies present in the sample.

(B) In an assay for anti-herpes virus antibodies, the herpes antigen ("$Ag_H$") is conjugated to glucose-6-phosphate dehydrogenase ("$Ag_H$-G6PDH"). A sample suspected of containing the antibodies is combined with AgH-G6PDH in a suitable medium. Rheumatoid factor bound to polyacrylamide particles is added and incubated. A ¼" polystyrene ball coated with anti-$Ag_H$ antibodies is added to the mixture. After suitable incubation, the ball is washed and contacted with glucose-6-phosphate and NAD. The signal produced by the appearance of NADH is directly related to the amount of $Ag_H$ that is bound to the surface, and is inversely related to the amount of anti-$Ag_H$ antibodies present in the sample.

As a matter of convenience, the reagents for use in the present invention can be provided in a kit for use in an assay method for detecting antibodies in a sample suspected of containing the antibodies. A typical kit of this invention comprises in a packaged combination: (i) an antigen that binds the antibodies to forman antigen:antibody complex, wherein the amount of antigen is Z, wherein Z is within the range of X to nX and Z is less than Y, where n is 5–1000, preferably 10–100, X is the minimum amount of antigen that can be reliably detected when there are no antibodies present in a sample and Y is the maximum expected amount of antibodies in the sample, (ii) a first binding agent that binds the complex without binding the antigen when the antigen is not part of the complex, and (ii) a second binding agent that selectively binds the antigen relative to binding the complex when the complex is bound to the first binding agent.

A preferred kit is useful for the detection of GAD autoantibodies and comprises GAD antigen and a receptor for the antigen:antibody complex as the first binding agent, which is bound to a soluble polymer. Another preferred kit is useful for the detection of insulin autoantibodies and comprises insulin and a receptor for the antigen:antibody complex as the first binding agent, which is bound to a soluble polymer.

Under appropriate circumstances one or more of the reagents in the kit can be provided in solution or as a dry powder, usually lyophilized, including excipients, which on dissolution will provide for a reagent solution having the appropriate concentrations for performing a method or assay in accordance with the present invention. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. As a matter of convenience, the reagents employed in the present invention can be provided in predetermined amounts. The kit can also contain written instructions on how to use the reagents and/or how to perform a particular assay, for example, in the form of a package insert. The invention is demonstrated further by the following illustrative examples.

ABBREVIATIONS

| | |
|---|---|
| AET | 2-Aminoethylisothiouronium bromide |
| $bGAD_{65}$ | Biotinylated GAD |
| BSA | Bovine Serum Albumin |
| EDTA | Ethylenediaminetetraacetic acid |
| ELISA | Enzyme linked immunosorbent assay |
| $GAD_{65}$ | Human recombinant glutamic acid decarboxylase, molecular weight 65,300 |
| HRP | Horseradish peroxidase |
| IDDM | Insulin Dependent Diabetes Mellitus |
| MAb | Monoclonal antibody |
| PBS | Phosphate buffered saline |
| PLP | Pyridoxal-5'-phosphate |
| RIA | Radioimmunoassay |
| RT | Room temperature |
| SAV | Streptavidin |
| SDS-PAGE | Sodium dodecyl sulfate-polyacrylamide gel electrophoresis |
| TCEP | Tris (carboxyethyl) phosphine |
| TMB | 3,3',5,5'-Tetramethylbenzidine |

PREPARATION OF MATERIALS

Parts and percentages herein are by weight unless otherwise indicated. Streptavidin-coated plates were made by standard techniques. The HRP-labeled anti-mouse antibodies were goat affinity purified antibodies to mouse IgG(γ-chain specific) (Kirkegaard & Perry Laboratories). All other chemicals were reagent grade and commercially available from sources such as Sigma and Fisher Chemical. All solutions were prepared in $H_2O$ and all reactions were performed under ambient conditions unless otherwise stated.

Buffer Composition

The composition of the Reaction Buffer was as follows: 20 mM Tris, pH 7.4, 150 mM NaCl, 0.5% TRITON® X-100, 10 mM benzamidine (15.7 mg/10 ml), Pefabloc (Pentapharm) at 2.4 mg/10 ml, Aprotinin (Pentapharm, 229,500 KIU/ml) at 50 µl/10 ml, and Pepstatin A (Sigma) at 0.2 mg/10 ml.

A. Expression and Purification of Human Recombinant $GAD_{65}$

Baculovirus cells expressing recombinant human $GAD_{65}$ were grown in a fermentor and harvested. The pellet was lysed using a glass homogenizer. After disruption, the cell lysate was centrifuged and washed, and the washed pellet was extracted to obtain membrane-bound $GAD_{65}$. This membrane extract was then loaded onto a Q Sepharose column and eluted with a KCl gradient. Enzymatically active fractions were pooled and loaded onto a Phenyl Sepharose column. Elution was done by a reverse phosphate gradient. Eluted fractions were assayed for enzymatic activity and tested for purity on a 10% SDS-PAGE. Fractions with a purity near 95% by protein staining were pooled. The pool was concentrated using Centriprep-30 (Amicon). Concentrated $GAD_{65}$ was made 50% in glycerol and frozen at −70° C.

1. Iodination of $GAD_{65}$

The iodination protocol was based on the commercially available Enzymobead kit (BioRad) to yield $[^{125}I]GAD_{65}$. The contents of the single reaction vial, sold with the kit, was first rehydrated. To this rehydrated vial was added 2 µl (1 µg) purified $GAD_{65}$, 5 µl (0.5 mCi) $^{125}I$, 25 µl of 1% β-D-glucose, 50 µl 0.2M sodium phosphate buffer pH 7.2, and 18 µl $H_2O$ (total vol 150 µl), followed by incubation. After reaction with the Enzymobeads, the contents of the vial were loaded directly onto a size-exclusion gel column, and 200 µl fractions were eluted with PBS, 1 mM AET, and 1 mM PLP. Fractions containing $^{125}I$ were identified by counting 1 µl aliquots.

Before use in the assay, $[^{125}I]GAD_{65}$ was preadsorbed using pooled normal human serum. 200 µl of $[^{125}I]GAD_{65}$ was mixed with 80 µl of Reaction Buffer, 100 µl of a pool of 8 IDDM negative control sera, and 20 µl of PBS. After an overnight incubation at 4° C., a 50% suspension of Protein A-Sepharose in PBS was added and incubated at 4° C. for 1 hr. This suspension was then microfuged, the supernatant collected, the pellet washed with 400 µl PBS, and the two supernatants pooled and saved in aliquots at −70° C.

2. Biotinylation of $GAD_{65}$

Purified $GAD_{65}$, 282 µg/450 µl in GAD buffer, pH 7.0, was adjusted to a pH of between 8.0 and 8.2 using 1 µl of 6N NaOH. The composition of the GAD buffer was 20 mol phosphate buffer (pH 6.8–7.0), 20 µM PLP, i mM AET, 1 mM EDTA, 0.1% TRITON X-100 and 10% glycerol. Then, 4 µl of 10 mM PLP and 5 µl of a 41 mg/ml solution of TCEP were added. After incubation on ice, biotinylation was carried out by adding 5 µl of iodoacetyl-LC-biotin (Pierce) for 3 hours at 4° C. in the dark. Unreacted biotin was separated by centrifugation. The biotin:$GAD_{65}$ ratio was determined to be approximately 3 to 5 mol biotin/mol $GAD_{65}$.

B. Mouse anti-$GAD_{65}$ antibodies

Mice were immunized with $GAD_{65}$, expressed and purified as described above, and MAbs raised according to standard procedures such as described in Milsrein and Kohler, supra.

The resulting MAbs were tested in a standard ELISA format and the best MAbs were selected based upon specificity for $GAD_{65}$.

A mixture of six anti-GAD MAbs was used in early assays to detect $bGAD_{65}$ bound to SAV-coated plates, each MAb at 1 pmol/µl in PBS plus 0.2% sodium azide. The final concentration of each MAb was 0.2 pmol/100 µl/well.

Later assays utilized only one anti-GAD MAb, which was labeled with HRP, thus eliminating the need for the HRP-labeled anti-mouse MAbs.

C. Protein A-Sepharose Suspension

Protein A-Sepharose (CL-4B, Sigma) was made into a 50% suspension in PBS and 0.1% azide.

D. MICROTRAK® Plate washer and Reader

The microtiter plate washer and reader are components of the MICROTRAK® EIA System (Syva Company). The wash solution used was the MICROTRAK Chlamydia EIA wash buffer: 0.559 g/ml trisodium citrate, 0.002 g/ml citric acid, 0.0182 ml/ml TWEEN® 20, 0.3175 ml/ml glycerol, pH 6.5–6.9. Each wash cycle was set for 300 µl/well ×5.

E. Human Serum Samples

Human sera used in these experiments were either control samples (no autoantibodies to $GAD_{65}$) or from patients with IDDM (autoantibodies to $GAD_{65}$ present), which were provided by Dr. Noel Maclaren at the University of Florida.

EXAMPLE I

Radioimmunoassay for $GAD_{65}$

To measure [$^{125}$I]$GAD_{65}$ bound by human sera, an overnight incubation was set up at 4° C. containing 6 μl of human sera, 10 μl (approximately 150,000 cpm) [$^{125}$I]$GAD_{65}$ preadsorbed with negative human sera in Reaction Buffer in a total volume of 25 μl. After overnight incubation, 50 μl of 50% Protein A-Sepharose was added and the incubation continued with gently shaking for 1 hr at 4° C. After Protein A-Sepharose incubation, the suspension was centrifuged at RT, washed 3× with 750 μl of ice cold 20 mM Tris, pH 7.4, 150 mM NaCl 0.5% TRITON X-100. Each wash was counted in a gamma counter and the pellet was counted after the final wash.

The following table summarizes typical counts found in each of the 3 wash fractions or bound in the pellet with negative sera or positive sera:

| Serum | Total Counts | Counts in Wash 1 | Wash 2 | Wash 3 | Counts bound |
|---|---|---|---|---|---|
| Neg | 188,037 | 140,940 | 12,280 | 2,236 | 2,130 |
| Pos | 196,063 | 118,324 | 12,804 | 4,536 | 11,230 |

Since the RIA uses an excess of radiolabeled material, a very small percentage of the input counts is finally obtained in the bound fraction. This is illustrated below, as the percent of radioactive $GAD_{65}$ that is bound:

| Serum | % Counts Bound |
|---|---|
| Neg | 1.1 |
| Pos | 5.7 |

Since the RIA format used a high excess of radiolabeled material, it was almost impossible to use the measurement of unbound material to accurately determine the amount of antibodies in the sample. For example, if only 5.7% of the [$^{125}$I]$GAD_{65}$ becomes bound to antibodies in the sample, then 94.3% remains free and would have to be measured. Using 100% [$^{125}$I]$GAD_{65}$ as a measure of the signal that would be produced by a negative sample, one would need to measure the difference between the signal produced by 100% and that produced by 94.3%. Such a small delta value would be difficult to accurately and reliably measure.

If $GAD_{65}$ could be depleted from the supernatant fluid sufficiently so that the difference between the total started with and that left in solution is a significant number, then this format could be used to determine the amounts of autoantibodies in IDDM sera. The present invention accomplishes this by using a minimal amount of labeled antigen and essentially "depleting" all of the labeled material from the supernatant. This depletion format allows for the use of high concentrations of serum in the initial reactions and also allows for the initial reactions to be in solution, similar to the RIA protocols. Unlike ELISA protocols that detect antibodies, the detection of $GAD_{65}$ results in very low background values even beginning with 50% serum concentrations.

The depletion assay of this invention thus involves a reaction between antigen and antibodies and the subsequent detection of antigen not complexed with antibodies. Thus, control healthy serum without anti-antigen antibodies will leave free antigen in the reaction mixture which will show a higher signal in subsequent measurements. Serum from patients with antibodies to the antigen will complex some or all of the input antigen leaving lower amounts of free antigen. In subsequent measurements, this will result in a low signal. Thus, it was expected that the amount of anti-antigen antibodies in a sample would be inversely correlated to the $A_{450}$ values in the depletion assay of this invention. As a result, in this assay a sample is judged "positive" when the $A_{450}$ value is below the cutoff value determined by the mean, minus 2 or 3 standard deviations, of several normal, control sera. This is in contrast to the typical RIA where a sample with a cpm value higher than the control mean cpm +2 or 3 SDs is judged as "positive". This is best illustrated in the following examples.

EXAMPLE II

Enzyme Immunoassay for $GAD_{65}$ (with centrifugation)

This example illustrates the general performance of the assay format of the present invention. The optimization of the GAD antigen concentration is illustrated in subsequent examples.

12 μl of human sera was mixed with 10 μl b$GAD_{65}$ (0.2 pmol per assay), 10 μl 15× Reaction Buffer and 18 μl $H_2O$ to a final volume of 50 μl. This was incubated overnight at 4° C.

100 μl of a 50% suspension of Protein A-Sepharose was added and incubated for 1 hour with gentle shaking on ice. This was then centrifuged at RT.

100 μl of supernatant fluid (containing unbound b$GAD_{65}$) was withdrawn from the Protein A-Sepharose pellet, diluted and transferred to a prewashed SAV-coated plate. After incubation for 1 hour at RT, with gentle agitation, the plate was washed on the MICROTRAK system.

100 μl of mouse anti-$GAD_{65}$ MAbs were added and incubated for 1 hour at 37° C., followed by washing as above.

100 μl of HRP-labeled anti-mouse antibodies were added and incubated for 1 hour at 37° C., followed by washing as above. TMB substrate was added and developed at RT for 30 minutes. Color development was stopped with 1N $H_2SO_4$ and read at 450 nm.

Seven out of nine patient sera were diagnosed correctly by this method. This is in contrast to conventional ELISA techniques which judged correctly only two out of the nine samples.

EXAMPLE III

Comparison with RIA

In order to assess the analytical performance of the assay of the present invention, comparison was made with test sera previously assayed by the RIA method. The primary objective was to determine if results from the two methods would correlate, irrespective of the nature of the sera, i.e., control or patient samples with a range of $GAD_{65}$ autoantibody titers.

The assay protocol was as described in Example II with the following modifications: serum (24 μl), bGAD$_{65}$ (20 μl containing 12 fmol), 5× Reaction Buffer (20 μl) and deionized H$_2$O (36 μl) were incubated overnight at 4° C. Protein A-Sepharose (200 μl of a 50% suspension) was added and further incubated at 4° C. for 1 hour. This was then centrifuged for 2 minutes at RT. The supernatant (180 μl) was carefully collected and two aliquots of 90 μl each were added to two SAV coated wells in a plate to generate duplicate values. The rest of the protocol was as explained in Example II.

The resulting clinical data indicated excellent correlation between the results of the present assay and the data obtained from the RIA.

EXAMPLE IV

Evaluation of Minimal of Antigen Concentration

A standard curve was run with the GAD antigen at different concentrations, and it was determined that, under the present conditions, the curve was linear up to about 0.1 pmol of antigen, and levels of less than 10 fmol could easily be detected. Initial assays utilized 2 pmol of the antigen, far above the minimum that could be detected. Therefore, the antigen concentration was gradually lowered in the hope of improving the ability to determine weak positive serum samples. The assay was repeated using a negative serum, a strong positive, and a weak positive (judged by RIA) using 2; 0.2; 0.1 and 0.01 pmol of antigen. It was clear that the ability to detect weak positives among IDDM samples improved by lowering the concentration of the GAD antigen.

EXAMPLE V

Optimization of Antigen Concentration

Several assays were run using a protocol similar to that of Example II, except that the control serum samples were utilized, which contained no GAD$_{65}$ autoantibodies. Readings were taken at 450 nm.

| [bGAD$_{65}$], fmol | Signal |
| --- | --- |
| 0 | 0.023 ± 0.003 |
| 0.075 | 0.064 ± 0.004 |
| 0.15 | 0.118 ± 0.003 |
| 0.20 | 0.224 ± 0.002 |

Measurement at 0 fmol of bGAD$_{65}$ was done to determine the level of background signal. Typically, the minimum amount of antigen that can be reliably detected when there are no antibodies present in a sample should be at least three standard deviations above the background signal. In the present instance the minimum amount of bGAD$_{65}$ that could be reliably detected when there are no antibodies present in a sample is that concentration which produced a signal of 0.023+3(0.003) or 0.032. To allow for a certain amount of variance, twice this number, i.e., a GAD concentration that produced a signal of 0.064, was selected as the value set for the minimum detectable amount of GAD$_{65}$. As can be seen from the table above, a signal of 0.064 corresponds to a minimum bGAD$_{65}$ concentration of 0.075 fmol. Additional optimization assays determined that 1.5 fmol worked particularly well, and this amount was used in Example VI. Subsequent studies of the minimum detectable level of GAD$_{65}$, similar to those described in this example, provided a four-fold improvement over the data presented above, providing a minimum detectable level of GAD$_{65}$ approximately four times less than the 0.075 fmol reported here.

EXAMPLE VI

Enzyme Immunoassay for GAD$_{65}$ (without centrifugation)

25 μl human sera in BSA buffer (10 mM KPhos, pH 7.0, 1 mM AET, 1 mM EDTA, 20μM PLP, 0.1% TRITON X-100, 10% glycerol and 1 mg/ml protease-free BSA) was mixed with 15 μl bGAD$_{65}$ (1.5 fmol per assay) and 10 μl 15× Reaction Buffer to a final volume of 50 μl . This was incubated for 2 hours at RT.

50 μl of Protein A-Dextran (1 to 25 dilution of stock in PBS) was added and incubated 1 hour at RT.

80 μl of supernatant fluid (containing unbound bGAD$_{65}$) was withdrawn and transferred to a prewashed SAV-coated plate. After incubation for 1 hour at RT, with shaking, the plate was washed on the MICROTRAK system.

100 μl of MAb(6G10)-HRP conjugate (1:320 dilution in Syva conjugate diluent, prewarmed at 37° C.) was added and incubated for 1 hour at RT, with shaking, followed by washing on the MICROTRAK system.

TMB substrate was added and developed at RT for 30 minutes. Color development was stopped with 1N H$_2$SO$_4$ and read at 450 nm. Performance of this method was comparable to that reported in Example II for the method using Protein A and Sepharose.

EXAMPLE VII

Comparative Evaluation

A blind study comparative evaluation of numerous GAD$_{65}$ immunoassays was presented in a report entitled the "Second International GAD Antibody Workshop" (1994), with the data compiled by the Royal Melbourne Hospital in Victoria, Australia. Forty assays were evaluated using 101 blind control and IDDM sera. Each participant remained unnamed but identified their respective assay by the format (RIA, ELISA and enzymic immunoprecipitation) and by the type of GAD (rat/human/porcine and native/recombinant). The assay of this invention (as described in Example VI) was also submitted for evaluation in this blind study.

The Royal Melbourne Hospital provided results to all participants, only identifying the assays by format and GAD type, as described above. The enzymic immunoprecipitation assays performed poorly, with the ELISAs performing somewhat better and the RIAs showing the best performance. The results of the assay of this invention are presented below, along with the average ELISA and RIA results:

| | % positive | | |
| --- | --- | --- | --- |
| Sample | ELISA | RIA | Invention |
| Control | 16.7 | 10.6 | 6.3 |
| IDDM patients | 36.5 | 76.2 | 82.0 |
| Preclinical IDDM patients | 82.5 | 97.1 | 100 |
| Other autoimmune diseases | 23.7 | 3.8 | 0 |

The assay method of the present invention gave fewer false positives on the control samples than both the RIA and the ELISA, 6.3%, compared to 10.6% and 16.7%, respectively. Similarly, the present invention did not give false positive results on the samples from patients with other autoimmune diseases. The RIA and ELISA gave 3.8% and 23.7% false positive readings, respectively.

The present invention also gave fewer false negatives than both the RIA and ELISA, indicating that 82% and 100% of the IDDM and preclinical IDDM patient samples, respectively, were positive. The RIA only indicated that 76.2% and 97.1% of the samples were positive, and the ELISA only indicated that 36.5% and 82.5% of the samples were positive.

While the present invention has been described with reference to the specific embodiments thereof, it will be understood by and obvious to those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of determining the presence or amount of specific antibodies to an antigen, in a sample suspected of containing said antibodies, said method comprising the steps of:
    (a) bringing together in an aqueous medium to form a mixture:
        (i) said sample,
        (ii) an antigen that binds said antibodies to form an antigen:antibody complex, wherein the molar amount of said antigen added to said medium is Z, wherein Z is within the range of X to nX and Z is less than Y, where n is 5–1000, X is the minimum molar amount of said antigen that can be reliably detected when there are none of said antibodies present in a sample and Y is the maximum expected molar amount of said antibodies in said sample, and
        (iii) a first binding agent that binds said complex and does not bind said antigen when said antigen is not part of said complex;
    (b) adding to said mixture a second binding agent that selectively binds said antigen relative to binding said complex when said complex is bound to said first binding agent; and
    (c) detecting said antigen bound to said second binding agent, the presence or amount thereof being related to the presence or amount of said antibodies in said sample.

2. The method of claim 1 wherein said first binding agent is selected from the group consisting of antibodies to immunoglobulins, complement factor C1q, rheumatoid factor, protein G and protein A.

3. The method of claim 2 wherein said first binding agent is bound to a suspendable solid phase or soluble polymer.

4. The method of claim 3 wherein said suspendable solid phase is a particle comprised of a material selected from the group consisting of polymers, ceramic and glass.

5. The method of claim 3 wherein said soluble polymer has a molecular weight of over 250,000.

6. The method of claim 1 wherein said detecting step involves the detection of enzyme activity, luminescence or light absorbance.

7. The method of claim 1 wherein said second binding agent is a receptor for said antigen and is bound to or capable of being bound to a support.

8. The method of claim 7 wherein said antigen is bound to a member of a signal producing system.

9. The method of claim 1 wherein said second binding agent is a first receptor that binds said antigen, which method further comprises contacting said mixture with a second receptor that binds said antigen, wherein at least one of said receptors is directly or indirectly bound to a label.

10. The method of claim 1 wherein said antigen is bound to a ligand and said second binding agent is a receptor for said ligand bound to a support.

11. The method of claim 10 which further comprises separating said support from said mixture and contacting said support with a receptor for said antigen.

12. The method of claim 1 wherein said antibodies are autoantibodies to glutamic acid decarboxylase or insulin.

13. A method of determining the presence or amount of antibodies against a certain antigen in a sample suspected of containing said antibodies, said method comprising the steps of:
    (a) bringing together in an aqueous medium:
        (i) said sample,
        (ii) an antigen that binds said antibodies to form an antigen:antibody complex, wherein the molar amount of said antigen added to said medium is Z, wherein Z is within the range of X to nX and Z is less than Y, where n is 5–1000, X is the minimum molar amount of said antigen that can be reliably detected when there are none of said antibodies present in a sample and Y is the maximum expected molar amount of said antibodies in said sample, and
        (iii) a first binding agent that binds said complex and does not bind said antigen when said antigen is not part of said complex;
    (b) contacting said medium with a second binding agent bound to a solid phase, wherein said second binding agent is a receptor that binds said antigen to form solid phase-bound antigen but does not bind said antigen:antibody complex;
    (c) detecting said antigen bound to said solid phase, the presence or amount thereof being related to the presence or amount of the antibodies in the sample.

14. The method of claim 13 wherein said first binding agent is selected from the group consisting of antibodies to immunoglobulins, complement factor C1q, rheumatoid factor, protein G and protein A.

15. The method of claim 14 wherein said first binding agent is bound to a suspendable solid phase or soluble polymer.

16. The method of claim 13 wherein said detection step comprises contacting said solid phase with one or more signal producing system members, and measuring the signal produced by said signal producing system members, the presence or amount thereof being related to the presence or amount of said antibodies in said sample.

17. The method of claim 16 wherein at least one of said signal producing system members is selected from the group consisting of fluorescers, enzymes, chemiluminescers, photosensitizers and suspendable particles.

18. A method of determining the presence or amount of antibodies in a sample suspected of containing said antibodies, said method comprising the steps of:
    (a) bringing together in an aqueous medium:
        (i) said sample,
        (ii) an antigen that binds said antibodies to form an antigen:antibody complex, wherein the molar amount of said antigen added to said medium is Z, wherein Z is within the range of X to nX and Z is less than Y, where n is 5–1000, X is the minimum molar amount of said antigen that can be reliably detected when there are none of said antibodies present in a sample and Y is the maximum expected molar amount of said antibodies in said sample, and (iii) a first binding agent that binds said complex and does not bind said antigen when said antigen is not part of said complex;

(b) adding to said medium a second binding agent comprised of two receptors that bind said antigen, where at least one of said receptors is unable to bind effectively to said complex when said complex is bound to said first binding agent; and (c) detecting the complex formed when said receptors bind said antigen, the presence or amount thereof being related to the presence or amount of said antibodies in said sample.

19. The method of claim 18 wherein said first binding agent is selected from the group consisting of antibodies to immunoglobulins, complement factor C1q, rheumatoid factor, protein G and protein A.

20. The method of claim 19 wherein said first binding agent is bound to a suspendable solid phase or soluble polymer.

21. The method of claim 18 wherein said detecting step involves the detection of luminescence or light absorbance.

22. The method of claim 21 wherein at least one of said receptors is bound to a detectable label selected from the group consisting of fluorescers, chemiluminescers and photosensitizers.

23. A method of determining the presence or amount of glutamic acid decarboxylase autoantibodies in a sample suspected of containing said autoantibodies, comprising the steps of:

(a) bringing together in an aqueous medium:
  (i) said sample,
  (ii) glutamic acid decarboxylase antigen that binds said autoantibodies to form an antigen:autoantibody complex, wherein the molar amount of said antigen added to said medium is Z, wherein Z is within the range of X to nX and Z is less than Y, where n is 5–1000, X is the minimum molar amount of said antigen that can be reliably detected when there are none of said antibodies present in a sample and Y is the maximum expected molar amount of said antibodies in said sample, and
  (iii) a first binding agent that binds said complex, wherein said first binding agent is a receptor for said autoantibodies and is bound to a material selected from the group consisting of a suspendable solid phase and a soluble polymer;

(b) adding to said medium a second binding agent that selectively binds said antigen relative to binding said complex when said complex is not separated from said medium; and (c) detecting the binding of said second binding agent to said antigen, the binding thereof being related to the presence or amount of said autoantibodies in the sample.

24. The method of claim 23 wherein said first binding agent is selected from the group consisting of antibodies to immunoglobulins, complement factor C1q, rheumatoid factor, protein G and protein A.

25. The method of claim 24 wherein said first binding agent is protein A and said soluble polymer is dextran.

26. The method of claim 23 wherein said detecting step involves the detection of enzyme activity, luminescence or light absorbance.

27. The method of claim 23 wherein said second binding agent is a receptor for said antigen and is bound to or capable of being bound to a support.

28. The method of claim 27 wherein said antigen is bound to a member of a signal producing system.

29. The method of claim 23 wherein said second binding agent is a first receptor for said antigen and which method further comprises contacting said medium with a second receptor that binds said antigen, wherein at least one of said receptors is bound to a member of a signal producing system.

30. The method of claim 23 wherein said antigen is bound to a ligand and said second binding agent is a receptor for said ligand bound to a support.

31. The method of claim 30 which further comprises separating said support from said medium and contacting said support with a second receptor for said antigen bound to a member of a signal producing system.

32. The method of claim 23 wherein the amount of said antigen added to said medium is 0.01–12.0 fmol.

33. The method of claim 32 wherein the amount of said antigen added to said medium is 0.025–7.5 fmole.

34. The method of claim 33 wherein the amount of said antigen added to said medium is 0.1–2.0 fmole.

35. In an assay for determining the presence or amount of antibodies in a sample suspected of containing said antibodies for use in the detection or monitoring of a human disease, comprising the steps of combining in an aqueous medium said sample and an antigen that binds said antibodies to form a mixture comprised of an antigen:antibody complex and free antigen; and detecting said free antigen, the presence or amount thereof being related to the presence or amount of said antibodies in the sample; wherein the improvement comprises using a molar amount of antigen that is Z, wherein Z is within the range of X to nX and Z is less than Y, where n is 10–100, X is the minimum molar amount of said antigen that can be reliably detected when there are no antibodies present in a sample and Y is the maximum expected molar amount of said antibodies in said sample.

36. In an assay for determining the presence or amount of antibodies in a sample suspected of containing said antibodies for use in the detection or monitoring of a human disease, comprising the steps of combining in an aqueous medium said sample and an antigen that binds said antibodies to form a mixture comprised of an antigen:antibody complex and free antigen; and detecting said free antigen, the presence or amount thereof being related to the presence or amount of said antibodies in the sample; wherein the improvement comprises adding a first binding agent that binds said complex but does not bind said antigen, followed by the addition of a second binding agent that binds said free antigen but does not bind antigen when it is part of said complex and detecting said free antigen but not said antigen:antibody complex.

37. A kit for use in a method for detecting antibodies, comprising in a packaged combination:

(a) an antigen that binds said antibodies to form an antigen:antibody complex, wherein the molar amount of said antigen is Z, wherein Z is within the range of X to nX and Z is less than Y, where n is 5–1000, X is the minimum molar amount of said antigen that can be reliably detected when there are no antibodies present in a sample and Y is the maximum expected molar amount of said antibodies in said sample, (b) a first binding agent that binds said complex without binding said antigen when said antigen is not part of said complex, said first binding agent being bound to a suspendable solid phase or a soluble polymer, and (c) a second binding agent that selectively binds said antigen relative to binding said complex when said complex is bound to said first binding agent, said second binding agent being bound to a label or a solid phase or a soluble polymer.

38. The kit of claim 37 wherein said antibodies are glutamic acid decarboxylase autoantibodies, said antigen is glutamic acid decarboxylase, and said first binding agent is a receptor for said complex and is bound to a soluble polymer.

39. The kit of claim 37 wherein said antibodies are insulin autoantibodies, said antigen is insulin, and said first binding agent is a receptor for said complex and is bound to a soluble polymer.

* * * * *